United States Patent [19]

Szabo

[11] Patent Number: 4,602,700
[45] Date of Patent: Jul. 29, 1986

[54] FAIL-SAFE MECHANICAL DRIVE FOR SYRINGE

[75] Inventor: Anthony W. Szabo, Livingston, N.J.

[73] Assignee: Daltex Medical Sciences, Inc., New York, N.Y.

[21] Appl. No.: 620,936

[22] Filed: Jun. 15, 1984

[51] Int. Cl.[4] ............................ F03G 1/06; F16H 1/20
[52] U.S. Cl. ..................................... 185/39; 74/411.5; 74/421 R; 185/38; 188/189; 192/8 R
[58] Field of Search .............. 74/411.5, 421 R, 421 A; 188/189; 192/8 R; 368/101; 185/38, 39

[56] References Cited

U.S. PATENT DOCUMENTS

| | | | |
|---|---|---|---|
| 343,778 | 6/1886 | Sueur | 188/189 |
| 986,414 | 3/1911 | Sundh | 74/421 R |
| 1,425,291 | 8/1922 | Seib | 188/189 |
| 1,817,216 | 8/1931 | Uggla | 74/421 A X |
| 2,900,021 | 8/1959 | Richtmyer et al. | 185/38 |
| 4,429,586 | 2/1984 | Dopfer et al. | 74/421 R |

*Primary Examiner*—Allan D. Herrmann
*Attorney, Agent, or Firm*—Lieberman, Rudolph & Nowak

[57] ABSTRACT

A high reliability drive arrangement produces a rate-controlled output displacement and is particularly suited for driving a medical infusion apparatus. Energy for producing the output displacement is derived from a wound spring which, in a preferred embodiment, is coupled to an output shaft by a redundant gearing system. First and second drive gears, and their associated pinions on the output shaft, are rotationally displaced with respect to one another to prevent alignment of potentially defective gear teeth and to align the teeth on one gear with the inter-tooth spacings on the other. The output shaft additionally engages a rate-control arrangement which governs the rate of rotation, and consequently, the rate of the displacement. The possibility of uncontrolled rotation is reduced by providing a safety arrangement having a safety gear plate which has fewer teeth than its associated drive gear. Additionally, an associated driven gear, which may be a pinion, is provided with at least one indentation which accommodates the teeth of the safety gear plate. A final gear in the rate-control system, which may be an escapement ratchet wheel, is provided with an associated centrifugal braking arrangement which operates to terminate rotation if a predetermined rate of rotation is exceeded.

17 Claims, 6 Drawing Figures

FAIL-SAFE MECHANICAL DRIVE FOR SYRINGE

BACKGROUND OF THE INVENTION

This invention relates generally to mechanical drive systems, and more particularly to a fail-safe spring drive system which is particularly suited for driving a syringe or other fluid infusion system over extended periods of time.

Known dispensers for infusing small doses of medical fluids over long periods of time are either bulky, and therefore not easily transportable, or powered by electrical motors. The motor-operated infusion systems require a source of power, such as electrical line power which confines the patient during the treatment, or batteries which are not reliable over long periods of time. Moreover, battery operated systems require the patient to maintain a relatively fresh supply of batteries since batteries have limited shelf lives.

It is a further problem with electrically operated dispenser systems that sophisticated and expensive insulation systems are required to prevent the introduction of even minute amounts of electrical energy into the vascular system of a patient. It is now known that even small amounts of electrical energy, illustratively on the order of microamperes, can adversely affect a patient's heart. Thus, in addition to affording only short periods of unattended operation, battery power infusion systems may be dangerous to the patient, particularly if the device is subject to wet conditions.

Some of the problems noted hereinabove associated with electrically operated dispenser systems are overcome by utilizing mechanical drive arrangements. Generally, the mechanical drive arrangements, in combination with a syringe, provide an infusion pump driven by a clock mechanism. The clock mechanisms are essentially of a conventional type wherein a plate-to-plate gearing system is provided a torque by a wound spring. The rate of rotation of the system, and consequently the rate of fluid infusion, is controlled by a conventional balance wheel and escapement system.

In addition to overcoming the disadvantages of electrical systems, mechanical drive systems provide all of the known economic advantages of time-released infusion systems. Thus, such mechanical systems permit continuous injection to the patient, thereby reducing labor requirements of hospital staff. Additionally, the automatic infusion systems reduce substantially the possibility of human failures, such as those which are produced when patient care personnel neglect or otherwise do not maintain prescribed injection schedules. Additionally, such mechanical systems provide the medical advantages of continuous injection, over cyclic injections, which conform more closely to the characteristics of fluid production systems within the patient.

It is a characteristic of conventional mechanical clockwork syringe drive systems that a high gear trained drive ratio, illustratively on the order of 1500:1 is required between the drive spring and escapement. Typically, the infusion apparatus is driven nearly directly by the spring. Four stages of spur gearing are generally required to achieve the required high gear ratios by plate-to-plate clockwork. When used in a clock, the four stages produce the hour, minute, and second hand drive, at the appropriate gear ratios. It is, however, a problem with such conventional clock technology that, when used as a clock, any failure of the gear drive mechanism is of relatively small consequence. At worst, the clock will show an incorrect time. Such is not the case, however, when a clock drive is utilized to pump a fluid intravenously into a patient. A failure of a clock mechanism under such circumstances may be catastrophic, and may result in a rapid release of the total spring energy into the infusion apparatus, illustratively a syringe, such that the patient receives a large, potentially lethal dosage of the infusion fluid. Additionally, conventional clock mechanisms are more prone to failure when used in an infusion system because substantially greater loads and stresses are required to drive a syringe than merely to rotate the hands of a clock.

In conventional plate-to-plate gear drive systems of the type which are generally provided in mechanical clock drives, a considerable shear stress is applied to the gear teeth since relatively few teeth along the perimeter of a gear are in engagement at any given time. Accordingly, each gear tooth is exposed to a substantial portion, and possibly the entire, drive load, resulting in a relatively high risk of failure. As noted hereinabove, the risk of failure is increased in infusion systems since the drive load is greater. Gear train failure in a plate-to-plate gear transmission system will almost always result in a catastrophic situation. For example, if the gear train fails at some point intermediate of the wound spring and the output shaft, the mechanism will stop and a patient may be denied the life-sustaining infusion. On the other hand, if the failure of the gear train occurs at a point intermediate of the output shaft and the escapement regulating system, then catastrophically rapid infusion may occur producing a potentially lethal overdose of the infusion fluid. Conventional clockwork systems, can therefore not be deemed to be sufficiently reliable in situations where human life may be at stake.

Failure of clockwork gear drive systems can occur from a variety of causes. For example, in a clockwork system, power is transmitted essentially from a plate gear to a pinion having substantially smaller diameter than the gear which drives it. Such pinions, however, are generally manufactured by known die casting or injection molded techniques. In such a manufacturing system, it may be possible that a defect exists in the mold or die which will result in a pinion tooth weakness which may be common to a batch of the devices. Of course, such weaknesses may also result from material or processing defects which are present in only one pinion. Such a weakness may result from an inclusion of foreign material during the casting or molding process. Such defects and weaknesses are generally not visible to the unaided eye, and can be detected with certainty only with expensive quality control systems such as x-ray imaging or ultrasonic systems.

It is, therefore, an object of this invention to provide a medical fluid infusion system which is inexpensive and simple to manufacture.

It is another object of this invention to provide a drive system for a syringe which is small, lightweight, portable, and easily attached to a patient.

It is also an object of this invention to provide a fluid dispensing system which is reliable over extended periods of operation.

It is a further object of this invention to provide a fail-safe arrangement for a fluid infusion system wherein uncontrolled operation of the fluid dispensing function is prevented.

It is also another object of this invention to provide a drive arrangement for a medical fluid dispensing system which does not require an external power source.

It is a yet further object of this invention to provide a medical fluid infusion system which does not require batteries for performing the fluid infusion function.

It is still a further object of this invention to provide a mechanical drive system which can provide a driving force at a controlled displacement rate.

It is additionally an object of this invention to provide a drive arrangement for a syringe utilizing only mechanically stored energy for performing the drive function.

It is yet another object of this invention to provide a high-reliability speed governor for a mechanical drive system.

It is yet a still further object of this invention to provide an operation indication for a vascular fluid infusion system.

It is additionally a further object of this invention to provide a substantially continuous power transmission arrangement whereby transmission torque is shared by a plurality of drive wheels.

Another object of this invention is to provide a drive system whereby the torque transmission capability between a drive shaft and an output shaft is substantially increased.

A further object of this invention is to provide a fail-safe system between an output shaft and a speed regulator thereof which prevents uncontrolled rotation of the regulator system in the event of tooth slippage in the regulator drive system.

A further object of this invention is to provide a fail-safe arrangement which prevents uncontrolled rotation of an escapement gear wheel.

SUMMARY OF THE INVENTION

The foregoing and other objects are achieved by this invention which provides a drive arrangement which is particularly suited for driving a medical fluid infusion system by providing a rate-controlled output displacement. Preferably, the drive arrangement is provided with a rotary drive means which provides a driving torque to a first shaft. In a preferred embodiment, the rotary drive means is provided with a spring member which is wound to store the energy which will be used to perform the driving function. A plurality of drive gears are arranged coaxially on the first shaft; the drive gears having a fixed rotational relationship with respect to one another. A second, or output, shaft is provided with first and second pinion members which communicate meshingly with the first and second drive gears, respectively. The first and second pinion members have a fixed rotational relationship with respect to one another which corresponds to the rotational relationship between the first and second drive gears. In accordance with the invention, there is further provided a rate control arrangement which governs the rate of operation of the drive arrangement. A control gear is fixed on the output shaft for communicating with the rate control arrangement so as to limit its rate of displacement in response to the rate control arrangement.

In one embodiment of the invention, the first and second drive gears are fixed coaxially on the first shaft and are rotationally displaced with respect to one another whereby the gear teeth on respectives ones of the drive gears are axially misaligned. In embodiments of the invention where only two such coaxial drive gears are provided and the drive gears have equal members of teeth, the drive gears are fixed onto the first shaft so as to have a rotational relationship therebetween which corresponds to a maximum axial misalignment between the gear teeth. Thus, in such an embodiment, a tooth on one of the drive gears is axially substantially aligned with a space between gear teeth on the other drive gear.

In accordance with the invention, the rate control arrangement is provided with first and second escapement ratchet wheels which are fixed coaxially on a ratchet wheel shaft and which, as in known escapement systems, rotate at a faster rate than the output shaft. A balance wheel shaft is provided with a balance wheel fixed axially thereon for oscillating rotatably at a substantially fixed, predetermined frequency. Additionally, first and second lever members with pins are arranged on a lever shaft so as to communicate between the first and second escapement ratchet wheels, respectively, and the balance wheel shaft. The lever members are of a generally known type each having a lever portion with two pin members extending orthogonally therefrom. A rotative coupling arrangement, which may include a gear reduction mechanism, rotatively couples the control gear to drive the ratchet wheel shaft. Thus, the rate of rotation of the output shaft is controlled in response to the frequency of oscillation of the balance wheel. In some embodiments, several balance wheels may be provided coaxially on the balance wheel shaft. However, the balance wheels are all fixed to the balance wheel shaft so as to rotate together. The first and second lever members are similarly fixed to rotate simultaneously with the lever shaft. Thus, there is provided a compound escapement arrangement whereby if one lever member is damaged, such as by the separation of a pin from the lever portion, the second lever member can perform the rate control function. Additionally, the undamaged lever member will drive the damaged lever member to prevent it from binding against its associated escapement ratchet wheel. The present compound system therefore performs the dual safety function of essentially eliminating the risk of escapement runaway, while preventing system jamming and stopping if a pin or lever is damaged or otherwise fails.

The rate control arrangement is provided with a frequency control system which governs the predetermined frequency of oscillation of the balance wheel. In one embodiment, the frequency of oscillation is governed to an extent by a spiral spring which is fixed substantially coaxially with the balance wheel shaft, and there is further provided a mechanism for adjusting the tension force in the spiral spring. Adjustment of the mechanism, and consequently the tension force in the spiral spring, affords adjustability of the frequency of oscillation of the balance wheel, and consequently the rate of displacement of the output shaft.

Overall system reliability is enhanced by using the aforementioned double drive gear arrangement communicating with separate pinion members on the output shaft. First, the system torque transmitting capability is improved by the fact that the effective face width or gear thickness corresponds to the sum of the respective face widths of the first and second drive gears. Additionally, since each such drive gear is in communication with a separate one of respective coaxial pinions, and, in accordance with the invention, the pinions are rotatively displaced with respect to one another, the probability that simultaneously engaged pinion teeth will be weak and fail, is substantially reduced. It is a problem with pinion members of the type which are die cast or injection molded that inclusions or voids may be introduced during the molding process, or there may be defects in the mold, which seriously weaken one or more pinion teeth. The rotational displacement of the first and second pinions with respect to one another minimizes the possibility that manufacturing defects, even if a molding defect affects each pinion, will cause simultaneous failures in each of the pinions resulting in a total loss of power transmission to the output shaft. The foregoing rotational displacement of the pinions, which can also apply to the drive gears, relates to a rotational displacement with respect to the particular orientation in which the pinions and gears were manufactured. Thus, a defect common to each of the pinions, for example, will not be in alignment between the first and second pinions, notwithstanding that the particular embodiment may have the pinion teeth of the first and second pinions in axial alignment.

The foregoing rotational displacement between the first and second drive gears and the first and second pinions, respectively, is provided to prevent catastrophic failure resulting from defects which may be common to a batch of such pinions. In accordance with the invention, however, there may be provided a further type of rotational displacement with respect to axial alignment of the gear teeth or pinion teeth. Such axial misalignment of the teeth, which is noted hereinabove, produces an effective increase in the number of teeth. Thus, the subject stacked gearing arrangement, in addition to having an increased effective face width, or effective gear thickness, also provides an effective increase in the number of teeth. In essence, the diametral pitch of the effective gear is increased, resulting in an increase in torque transmission capability.

The foregoing gearing system is proposed for improving the reliability of power transmission to the output shaft. However, the present invention further provides an arrangement whereby the possibility of uncontrolled rotation of the output shaft is essentially eliminated. In accordance with this aspect of the invention, a gear and its associated pinion are arranged to have a pitch relationship corresponding to a ratio of integers. In a situation such as the present one where the gear shafts drive the pinion shafts, a wheel on the gear shaft will have at least one tooth which is received by an indentation in the wheel on the pinion shaft. The pinion wheel has a number of indentations which corresponds to the smallest denominator after the ratio of integers is reduced arithmetically. The tooth of the gear wheel extends radially outward for a distance which exceeds the clearance between the gear and pinion wheels. Thus, if a displacement occurs resulting from broken or missing teeth in a stacked gear or pinion which actually transmits the torque, a rotational shift will occur whereby the tooth on the gear wheel will not be synchronized rotationally with the indentation in the pinion wheel, thereby causing the tooth to jam against the outer surface of the pinion wheel. Preferably, the pinion wheel has a number of indentations distributed therearound; the number being one-third or less the number of pinion teeth on its associated driven pinion. Thus, if up to three pinion teeth are damaged on the driven pinion, the gear wheel tooth will not drive the pinion wheel. Preferably, the configuration of the tooth of the gear wheel and the configuration of the indentations in the pinion wheel may be such that displacement by an angular distance corresponding to only one pinion tooth of the associated driven pinion will prevent engagement and result in jamming. In certain embodiments, however, it may be desirable to configure the indentation of the pinion to accommodate the gear wheel tooth even if it is displaced rotationally by an angular distance corresponding to one gear tooth, of the stacked driving gear. By this arrangement, the drive arrangement will continue to operate properly even if one, and possibly two, pinion or gear teeth have failed, but will prevent operation when three teeth have failed.

The foregoing arrangement of jamming a potentially catastrophic gear displacement on the regulator side of the gear drive system has the added advantage that the pinion wheel does not have pinion teeth, in the conventional sense, thereby eliminating the dangers associated with pinion teeth defects. This arrangement is suitable for each gear-pinion engagement and the regulator side of the mechanical drive. The present invention therefore contemplates within its scope a fail-safe arrangement for preventing uncontrolled rotation of the escapement ratchet wheel, which does not communicate with a pinion. In a preferred embodiment, a safety wheel is fixed onto the shaft of the escapement ratchet wheel so as to rotate simultaneously therewith. A centrifugal throwout mechanism is installed on the safety wheel, which mechanism is extended radially outward of the safety wheel in response to an uncontrolled rotation and acceleration of the escapement ratchet wheel. At least one stationary member is provided for engaging with the radially extended centrifugal throwout mechanism. Such an engagement prevents rotation of the safety wheel, and consequently the escapement ratchet wheel.

In one embodiment of the invention, the centrifugal throwout mechanism may include a spring-loaded throwout member which is maintained in a radially inward position by an inwardly urging spring. However, a centrifugal force resulting from uncontrolled rotation is sufficient to overcome the radially inward directed spring force, thereby permitting the radially outward extension of the centrifugal throwout member. The stationary member which couples with the radially extended centrifugal throwout mechanism may be a post or wedge-shaped brake which is fixed to a stationary chassis or housing member. Thus, the last link in the regulating drive train, i.e., the escapement ratchet wheel, is protected from uncontrolled or excessively rapid rotation.

In a further embodiment, the escapement arrangement is configured so as to tick rather loudly as an indicator of its operability. Additionally, the balance wheel may be arranged in the vicinity of an opening, or window, in the case of the unit to permit visual inspection of the operation of the device.

BRIEF DESCRIPTION OF THE DRAWINGS

Comprehension of the invention is facilitated by reading the following detailed description in conjunction with the annexed drawings, in which.

DETAILED DESCRIPTION

Figure 1:
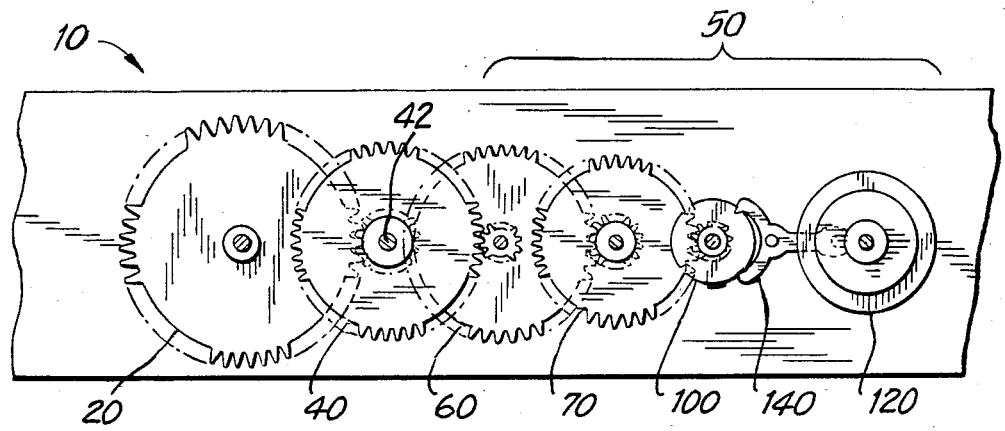
FIG. 1 is a partially schematic, simplified representation of an embodiment of the invention having an aligned gear train.

FIG. 1 is a simplified, partially schematic representation of a mechanical drive system 10 having a drive stack 20 which, as will be described hereinbelow, supplies the mechanical energy to effect the driving function. Drive stack 20 is in mechanical communication with an output stack 40 having an output shaft 42 which couples with the mechanism to be driven (not shown).

In this embodiment of the invention, output stack 40 is mechanically engaged with a speed-control system 50 which operates to limit the rate of rotation of output shaft 42. In this specific illustrative embodiment, speed-control system 50 is formed of first and second reduction gear stacks 60 and 70, respectively. Second reduction gear stack 70 drives an escapement ratchet wheel stack 100 which is coupled to a balance wheel stack 120 via a lever stack 140.

Figure 2:
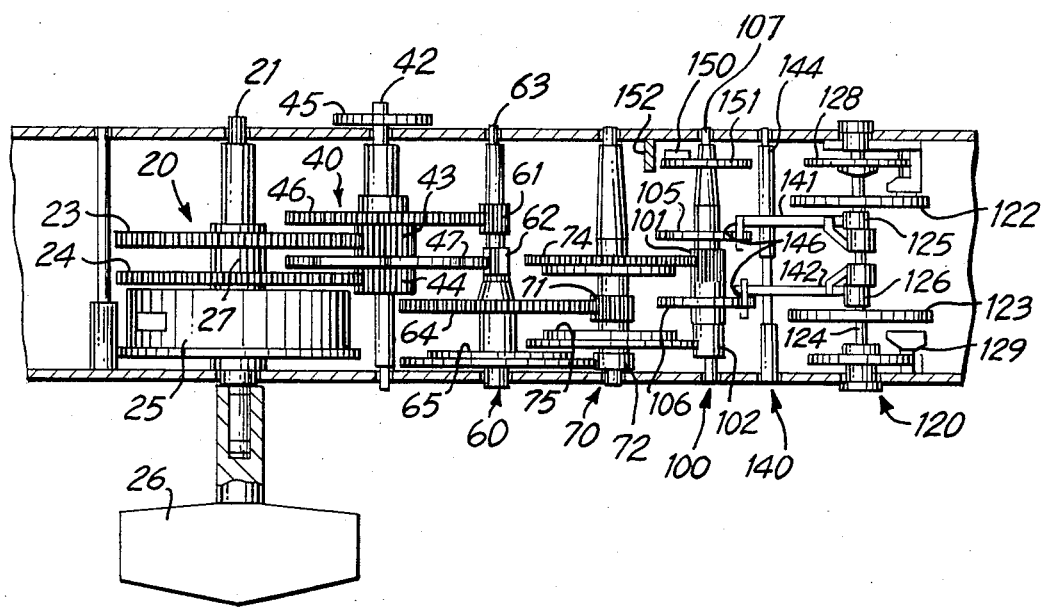
FIG. 2 is a simplified, partially schematic representation of a side view of the embodiment represented in FIG. 1.

FIG. 2 is a side view of an embodiment of the invention corresponding to that shown in FIG. 1. The simplified representation of FIG. 2 shows drive stack 20 formed of a drive shaft 21 on which is coaxially fixed a pair of drive gears 23 and 24. Additionally, a mainspring assembly 25 is fixed coaxially to drive shaft 21 via a ratchet arrangement (not shown) which permits the mainspring assembly to be wound by rotary manipulation of a wind key 26. In a known manner, mainspring assembly 25 is coupled to a structural member (not shown) in a known manner to permit the storage of energy in the mainspring assembly.

Drive gears 23 and 24 are fixed to the drive shaft by a collar 27 which secures the drive gears by any of several known means. Such securing may be achieved by pressure fit, crimping, slot and key, spot welding, bonding, etc. In the present situation where high reliability of operation is required, it is essential that the drive gears be fixed securely to the drive shaft.

Mechanical energy stored in mainspring assembly 25 is transferred to output shaft 42 by the meshing engagement of drive gears 23 and 24 with pinions 43 and 44, respectively, which are fixed onto output shaft 42 by any of the means described hereinabove. In this specific illustrative embodiment, an output gear 45 is fixed to output shaft 42 in a manner which will permit the driving of a utilization mechanism (not shown). As indicated hereinbefore, such a utilization mechanism may include a syringe which is desired to be driven over an extended period of time.

Figure 3:
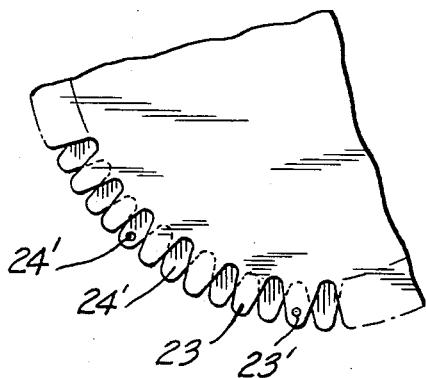
FIG. 3 is a fragmented representation of a stacked drive gear arrangement which can be used advantageously in the practice of the invention.

FIG. 3 is a fragmented representation of a top plan view of drive gears 23 and 24. As previously indicated, the drive gears are arranged coaxially with respect to one another, and may additionally have their respective gear teeth aligned axially. However, in accordance with the invention, gear teeth 23 and 24 may be rotationally displaced with respect to one another in several ways. First, a gross rotational displacement insures that weaknesses in the gear teeth resulting from manufacturing defects are not placed in alignment with one another, but are located at different locations along the rotation cycle. For example, assuming for the moment that drive gears 23 and 24 are identical to one another, and in fact manufactured via the same mold or die, respectively corresponding gear teeth are identified and the gears are rotated so that such corresponding gear teeth are displaced from one another. In FIG. 3, drive gear 23 has a specifically identified gear tooth 23', and drive gear 24 has a similar corresponding gear tooth 24'. During manufacture, the identified teeth, 23' and 24', which correspond to the same tooth in the mold or die used during manufacture. Upon instalation onto drive shaft 21, in the present embodiment, the drive gears are displaced so that gear teeth 23' and 24' are not in alignment. Preferably, such corresponding gear teeth should be displaced by an arc which corresponds in length to the distance of approximately three gear teeth. Of course, it would be advantageous if gear teeth 23' and 24' were approximately diametrically opposed from one another.

A second component of rotational displacement shown in FIG. 3 corresponds to axial alignment between the gear teeth of one drive gear with the intertooth spacing of the other gear. Such a displacement, as noted hereinbefore, appears as a doubling of the effective number of gear teeth, resulting in an increase in the torque transmission capability of the drive stack. Thus, a substantial increase in torque capacity, and consequently reliability, is achieved by the combination of the stack drive gears, resulting in a net doubling of the face width of the gears, and the second rotational displacement which effectively doubles the number of gear teeth.

Returning to FIG. 2, drive gears 23 and 24 are meshingly engaged with respective pinions 43 and 44. In one particularly advantageous embodiment of the invention, pinions 43 and 44 are subjected to rotational displacement with respect to one another. preferably in both senses discussed hereinabove with respect to the drive gears shown in FIG. 3. Thus, pinions 43 and 44 will be grossly rotationally displaced so that corresponding gear teeth are axially substantially misaligned, while the pinion teeth of one pinion are axially aligned with the inter-tooth spacings of the other pinion. Thus, meshing communication between the pinions and drive gears is achieved in a reliable manner.

In addition to pinions 43 and 44, output stack 40 is provided with a pair of gear plates 46 and 47 which are fixed coaxially to output shaft 42. In one embodiment, gear plates 46 and 47 correspond to gears similar to drive gears 23 and 24 described hereinabove. In such an embodiment, the gear plates would be provided with respective rotational displacements as described with respect to FIG. 3. Gear plates 46 and 47 communicate with pinions 61 and 62 which are coaxially fixed on shaft 63 of first reduction gear stack 60. Pinions 61 and 62 would be rotationally displaced in the manner described hereinabove with respect to pinions 43 and 44 of the output stack.

Figure 4:
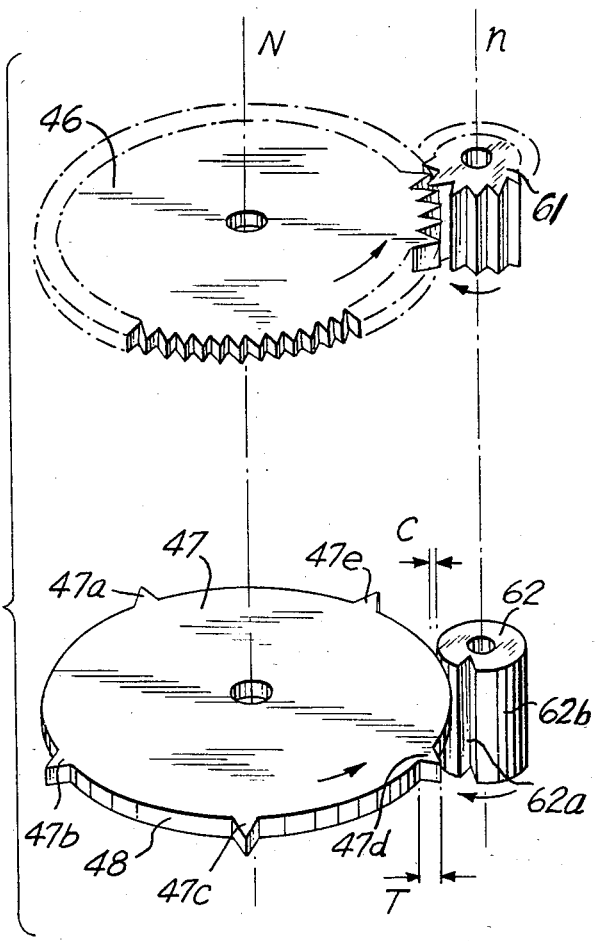
FIG. 4 is a simplified, partially exploded representation of a fail-safe system for preventing uncontrolled rotation of the gear train resulting from defective pinion or gear teeth.

In a further embodiment of the invention, which is shown in FIG. 4, gear plates 46 and 47 are shown in a simplified, exploded view. Gear plate 46 is meshingly engaged with pinion 61, the gear tooth to pinion tooth ratio corresponding to N:n. In the particular embodiment of FIG. 4, gear plate 47 and its associated pinion 62 are stacked coaxially with gear plate 46 and pinion 61, and share their pitch ratio. In this specific illustrative embodiment, the ratio of gear teeth N to pinion teeth n corresponds to 5:1. Accordingly, gear plate 47 is provided with five relatively large teeth 47a to 47e, while pinion 62 is provided with a single indentation 62a. Gear plate teeth 47a–47e are configured so as to be accommodated in pinion indentation 62a whereby only minimal contact is achieved between the exterior side surface of the gear plate teeth and the interior surface of the pinion indentation. Since gear plates 46 and 47, and pinions 61 and 62 are fixed on respective shafts, the gear plates and pinions rotate synchronously, and therefore, during normal operation, gear plate 47 does not drive pinion 62. Instead, this plate and pinion is rotated in response to the rotation of gear plate 46 and pinion 61, whereby gear plate 46 drives pinion 61. A first advantage which is present in the subject arrangement is that no driving friction results from the essentially non-communicating accommodation of gear plate teeth 47a–47e within pinion indentation 62a.

Gear plate 47 and pinion 62 rotate in directions indicated by their respectively associated arrows. In FIG. 4, gear plate tooth 47d is about to be accommodated within the pinion indentation, upon continuation of rotation in the indicated directions. In the event of a failure of one or more teeth on either gear plate 46 or pinion 61, a rotational displacement will occur between shafts 42 and 63 (not shown in this figure), as a result of a tooth slippage. As a result of such a rotational displacement between gear plate 66 and pinion 61, gear plate 47 and pinion 62 will be similarly displaced. However, gear plate teeth 47a–47e will not be synchronized with the rotation of pinion 62 so as to be accommodated within pinion indentation 62a. Such desynchronization causes one of the teeth 47a to 47e to jam against outer surface 62b of pinion 62. Such jamming results from the fact that the clearance C between an annular edge face 48 of gear plate 47 and outer surface 62b of the pinion is less than the radial length T of each gear plate tooth. Although five teeth, 47a to 47e, are shown in this embodiment, only one such tooth is required in the practice of the invention.

In this particular embodiment of the invention, first reduction gear stack 60 is provided with gear plates 64 and 65 which communicate with pinions 71 and 72, respectively, of second reduction gear stack 70. Additionally, a pair of gear plates 74 and 75, which are coaxially arranged in second reduction gear stack 70 engage with a pair of respective pinions 101 and 102 which are coaxially aligned in escapement ratchet wheel stack 100.

In accordance with the invention, first and second reduction gear stacks 60 and 70 of speed control system 50 may each include a stacked combination of a drive gear arrangement and a safety gear arrangement, similar to gear plates 46 and 47, respectively, discussed hereinabove with respect to FIG. 4. Thus, the safety features inherent in the stack's combination of gear plates 46 and 47 are also present in gear stacks 60 and 70, so that protection from uncontrolled rotation is provided in the gear train up to the communication between stacked gear plates 74 and 75 of second reduction gear stack 70 and pinions 101 and 102 of escapement ratchet wheel stack 100.

In this embodiment of the invention, the possibility of uncontrolled rotation of the escapement ratchet wheel stack is reduced by a compound escapement arrangement wherein first and second ratchet wheels, 105 and 106, respectively, are arranged coaxially on a ratchet wheel shaft 107. Preferably, ratchet wheels 105 and 106 are fixed onto ratchet wheel shaft 107 such that their respective ratchet teeth are axially aligned.

The rate of rotation of ratchet wheels 105 and 106 is controlled by a pair of levers 141 and 142 which are fixed onto a lever shaft 144 to form lever stack 140. The levers oscillate in response to the frequency of oscillation of balance wheel stack 120. In this embodiment, balance wheel stack 120 is provided with first and second balance wheels 122 and 123, respectively, which are fixed onto a balance wheel shaft 124. In a known manner, cams 125 and 126 cause levers 141 and 142 to oscillate such that the levers permit the controlled rotational escapement of ratchet wheels 105 and 106. The communication between the ratchet wheels and the levers is achieved by pins 146 which are fixed to the levers and extend substantially orthogonally therefrom. It is known that, in a single lever and ratchet wheel escapement system, the loss of one or both of the pins from the lever causes the escapement arrangement either to bind or rotate uncontrollably. This situation is essentially prevented in accordance with the present invention because the compounding of the escapement systems would require several such pins to fail if the escapement is either to jam or rotate uncontrollably.

The foregoing notwithstanding, the present invention, provides a centrifugal arrangement 150 which prevents uncontrolled rotation of the escapement ratchet wheel stack. Preferably, centrifugal arrangement 150 is arranged on ratchet wheel shaft 107 and may include a base member 151 which rotates therewith, and a stop 152 which is stationary.

Figure 5:
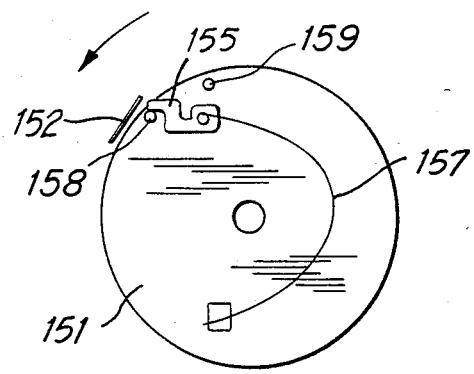
FIG. 5 is a highly simplified representation of an illustrative centrifugal safety arrangement during controlled shaft rotation.
Figure 6:
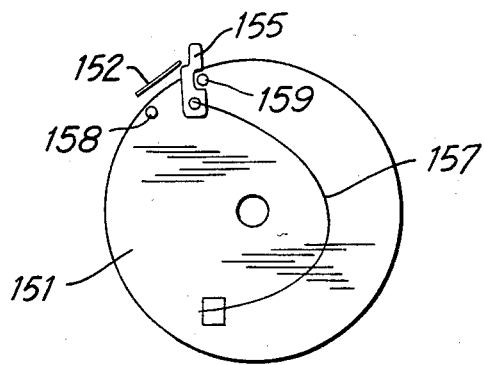
FIG. 6 is a representation of the illustrative embodiment of FIG. 5 during rapid or uncontrolled rotation.

FIGS. 5 and 6 illustrate an illustrative mechanism which operates centrifugally to prevent uncontrolled rotation of the escapement ratchet wheel stack. FIG. 5 shows an embodiment of a mechanism in schematic form while base member 151 is rotationally either stationary or moving at normal operating speeds. FIG. 6 shows the mechanism after having experienced a substantial centrifugal acceleration such that a centrifugal member 155 is displaced radially with respect to base member 151 so that it engages stop 152. The centrifugal member, as shown in FIG. 5, does not extend radially outwardly sufficient to communicate with stop 152 during normal or lower operating speeds. Of course, any of several other arrangements for effecting a centrifugal braking system may be utilized in the practice of the invention, and may include a resilient member for urging centrifugal member 155 radially inward of base member 151, such as wire spring 157. From FIGS. 5 and 6, it can be seen that pin 158 supports member 155 in a resting position, while pin 159 supports member 155 when radially displaced with respect to base member 151.

It is to be understood that although two levers 141 and 142 are shown, the balance wheel stack will function properly if only one balance wheel is arranged thereon. In the present embodiment, two hairspring arrangements 128 and 129 are provided and operate simultaneously to control the rate of oscillation of the balance wheel stack. However, only one such hairspring arrangement need be provided in some embodiments of the invention. Persons of ordinary skill in the art, in light of this teaching, can configure the balance wheel stack to oscillate at a proper frequency while using only one balance wheel or only one hairspring arrangement.

Although the invention has been described in terms of specific embodiments and applications, persons skilled in the art, in light of this teaching, can generate additional embodiments without exceeding the scope or departing from the spirit of the claimed invention. Accordingly, it is to be understood that the drawings and the descriptions in this disclosure are proffered to fascilitate comprehension of the invention and should not be construed to limit the scope thereof.

What is claimed is:

1. A drive arrangement for producing a rate-controlled output displacement, the drive arrangement comprising:
    rotary drive means for providing a driving torque to a first shaft;
    first and second drive gears arranged coaxially with said first shaft, each of said first and second drive gears having a fixed rotational relationship with respect to each other;
    a second shaft for producing the output displacement;
    first and second pinion members fixed coaxially to said second shaft and communicating with said first and second drive gears, respectively, for transmitting a torque to said second shaft, said first and second pinion members having a fixed rotational relationship with respect to each other, said rotational relationship between said first and second pinion members corresponding, in part, to said relationship between said first and second drive gears;
    rate control means for fixing a time rate; and
    control gear means fixed coaxially to said second shaft for coupling said second shaft to said rate control means wherein said rate control means comprises:
    first and second ratchet wheels fixed coaxially on a common ratchet wheel shaft;
    a balance wheel fixed coaxially on a balance wheel shaft for oscillating rotatively at a predetermined frequency; and
    first and second lever members arranged coaxially on a common lever shaft whereby said first and second lever members rotate simultaneously with said common lever shaft, for controlling a rate of rotation of said first and second ratchet wheels in response to said predetermined frequency of oscillation of said balance wheel.

2. The drive arrangement of claim 1 wherein said first and second drive gears are rotationally displaced with respect to one another whereby gear teeth on respective ones of said first and second drive gears are axially misaligned.

3. The drive arrangement of claim 2 wherein the first and second drive gears have equal numbers of gear teeth, said rotational relationships between said first and second drive gears and said first and second pinion members corresponding to maximum axial misalignment between respective gear teeth.

4. The drive arrangement of claim 3 wherein said rate control means further comprises rotative coupling means for rotatively coupling said control gear means to said common ratchet wheel shaft.

5. The drive arrangement of claim 4 wherein said rotative coupling means comprises gear reduction means whereby said common ratchet wheel shaft rotates at a faster rate than said control gear means.

6. The drive arrangement of claim 5 wherein there is further provided frequency control means for governing said predetermined frequency of oscillation of said balance wheel.

7. The drive arrangement of claim 6 wherein said frequency control means comprises:
    spiral spring means fixed substantially coaxially on said common balance wheel shaft; and
    means for adjusting a tension force in said spiral spring means.

8. A drive arrangement for producing a rate-controlled output displacement, the drive arrangement comprising:
    rotary drive means for providing a driving torque to a first shaft;
    first and second drive gears arranged coaxially with said first shaft, each of said first and second drive gears having a fixed rotational relationship with respect to each other;
    a second shaft for producing the output displacement;
    first and second pinion members fixed coaxially to said second shaft and communicating with said first and second drive gears, respectively, for transmitting a torque to said second shaft, said first and second pinion members having a fixed rotational relationship with respect to each other, said rotational relationship between said first and second pinion members corresponding in part to said relationship between said first and second drive gears;
    rate control means for fixing a time rate; and
    control gear means fixed coaxially to said second shaft for coupling said second shaft to said rate control means; and
    wherein there is further provided runaway safety means for preventing uncontrolled rotation of said second shaft; and
    wherein said runaway safety means comprises;
    safety wheel means having a predetermined pitch diameter D and at least one tooth member extending radially outward beyond said predetermined pitch diameter D for a predetermined distance t; and
    safety pinion means having a predetermined pitch diameter d and at least one receiver indentation extending radially inwardly therefrom for accomodating said tooth member of said safety wheel means, a clearance distance between said safety wheel means and said safety pinion means being less than said predetermined distance t.

9. The drive arrangement of claim 8 wherein said first and second drive gears are identical to one another and fixed in a rotative orientation with respect to one another whereby corresponding gear teeth thereon are rotatively displaced by an angular distance corresponding to at least three consecutive gear teeth.

10. The drive arrangement of claim 8 wherein said first and second pinion members are identical to one another and fixed rotatively with respect to one another whereby corresponding pinion teeth thereon are rotatively displaced by an angular distance corresponding to at least three consecutive pinion teeth.

11. A fail-safe arrangement for preventing desynchronization between a drive gear shaft having a drive gear fixed thereon and a driven gear shaft having a driven gear fixed thereon, the drive gear having a pitch diameter D with a number n of gear teeth arranged therearound, the driven gear having a pitch diameter d with a number n of gear teeth arranged therearound, the fail-safe arrangement further comprising:
    safety drive gear means fixed to the drive gear shaft coaxially with the drive gear, said safety gear drive means having a number N' of gear teeth, where N' is less than N; and safety driven gear means fixed to the driven gear shaft coaxially with the driven gear, said safety driven gear means having a number n' of gear teeth, where n' is less than n.

12. The fail-safe arrangement of claim 11 wherein a ratio of N/n of numbers of teeth is reduced to an integer I.

13. The fail-safe arrangement of claim 12 wherein said ratio N/n of numbers of teeth is said integer I plus an arithmetically reduced fraction a/b, where a and b are integers, said safety driven gear means having at least b teeth.

14. The fail-safe arrangement of claim 11 wherein said safety drive gear means and said safety driven gear means have a predetermined clearance therebetween, said gear teeth of said safety drive gear means extending radially outward for a distance greater than said predetermined clearance.

15. The fail-safe arrangement of claim 11 wherein there is further provided centrifugal safety means fixed to said driven gear shaft for preventing rotation thereof above a substantially predetermined rate of rotation.

16. The fail-safe arrangement of claim 15 wherein said centrifugal safety means comprises:

rotatable base means arranged parallel and coaxially with the driven gear;

a centrifugal member arranged on said rotatable base means for moving radially outward therefrom in a response to a rate of rotation of said rotatable base means; and a stop member arranged to be stationary in the vicinity of said rotatable base means for engaging said centrifugal member when said rotatable base means is rotated above said substantially predetermined rate of rotation.

17. The fail-safe arrangement of claim 16 wherein there is further provided resilient means for urging said centrifugal member radially inward of said rotatable base means.

* * * * *